United States Patent
Lee

(10) Patent No.: US 9,567,385 B2
(45) Date of Patent: Feb. 14, 2017

(54) MODIFIED ACIDIC FIBROBLAST GROWTH FACTORS AND COMPOSITION THEREOF

(71) Applicant: EU SOL Biotech Co., Ltd., New Taipei (TW)

(72) Inventor: Ya-Hui Lee, New Taipei (TW)

(73) Assignee: EU SOL BIOTECH CO., LTD., New Taipei (TW)

( * ) Notice: Subject to any disclaimer, the term of this patent is extended or adjusted under 35 U.S.C. 154(b) by 0 days.

(21) Appl. No.: 14/508,118

(22) Filed: Oct. 7, 2014

(65) Prior Publication Data

US 2015/0099701 A1  Apr. 9, 2015

Related U.S. Application Data

(60) Provisional application No. 61/887,619, filed on Oct. 7, 2013.

(51) Int. Cl.
*C07K 14/50* (2006.01)
*A61K 38/18* (2006.01)

(52) U.S. Cl.
CPC ......... *C07K 14/501* (2013.01); *A61K 38/1825* (2013.01)

(58) Field of Classification Search
None
See application file for complete search history.

(56) References Cited

U.S. PATENT DOCUMENTS 7,956,033 B2 * 6/2011 Cheng et al. .................. 514/9.1

* cited by examiner

*Primary Examiner* — Marianne P Allen
(74) *Attorney, Agent, or Firm* — WPAT, P.C., Intellectual Property Attorneys; Anthony King

(57) ABSTRACT

The present invention provides acidic fibroblast growth factor (aFGF) composition, comprising: (i) aFGF of SEQ ID NO: 1, (ii) aFGF of SEQ ID NO: 1 having an N-terminal phosphogluconoylation, (iii) aFGF of SEQ ID NO: 1 having an N-terminal gluconoylation, (iv) aFGF of SEQ ID NO: 2 and (v) aFGF of SEQ ID NO: 3, or a combination thereof. Also provided is a modified acidic fibroblast growth factor (aFGF) which has an N-terminal phosphogluconoylation or gluconoylation.

4 Claims, 5 Drawing Sheets

SEQUENCE LISTING

```
<160> NUMBER OF SEQ ID NOS: 3

<210> SEQ ID NO 1
<211> LENGTH: 135
<212> TYPE: PRT
<213> ORGANISM: Artificial Sequence
<220> FEATURE:
<223> OTHER INFORMATION: Peptide modified from Homo sapiens
      Acid-Fibroblast Growth Factor (a-FGF)

<400> SEQUENCE: 1

Ala Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
                20                  25                  30

Ser Asp Gln His Ile Gln Leu Gln Leu Ser Ala Glu Ser Val Gly Glu
            35                  40                  45

Val Tyr Ile Lys Ser Thr Glu Thr Gly Gln Tyr Leu Ala Met Asp Thr
50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
    130                 135

<210> SEQ ID NO 2
<211> LENGTH: 135
<212> TYPE: PRT
```

```
<213> ORGANISM: Artificial Sequence
<220> FEATURE:
<223> OTHER INFORMATION: Peptide modified from Homo sapiens
      Acid-Fibroblast Growth Factor (a-FGF)

<400> SEQUENCE: 2

Ala Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Lys Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
            115                 120                 125

Pro Leu Pro Val Ser Ser Asp
            130                 135

<210> SEQ ID NO 3
<211> LENGTH: 135
<212> TYPE: PRT
<213> ORGANISM: Artificial Sequence
<220> FEATURE:
<223> OTHER INFORMATION: Peptide modified from Homo sapiens
      Acid-Fibroblast Growth Factor (a-FGF)

<400> SEQUENCE: 3

Ala Lys Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
            115                 120                 125

Pro Leu Pro Val Ser Ser Asp
            130                 135
```

MODIFIED ACIDIC FIBROBLAST GROWTH FACTORS AND COMPOSITION THEREOF

FIELD OF THE INVENTION

The present invention relates to a modified acidic fibroblast growth factor (aFGF) with phosphogluconoylation or gluconoylation. The present invention also relates to an aFGF composition, comprising: (i) aFGF of SEQ ID NO: 1, (ii) aFGF of SEQ ID NO: 1 having an N-terminal phosphogluconoylation, (iii) aFGF of SEQ ID NO: 1 having an N-terminal gluconoylation, (iv) aFGF of SEQ ID NO: 2 and (v) aFGF of SEQ ID NO: 3, or a combination thereof.

BACKGROUND OF THE INVENTION

Acidic fibroblast growth factor (aFGF), which influences the proliferation and differentiation of various cell types in vitro, were originally isolated as single chain proteins from neural tissue, including whole brain and hypothalamus. aFGF is a heparin-dependent mitogen and it can strongly bind on all four known FGF receptors and their spliced form. It can be localized within specific subsets of neurons associated with motor and sensory functions, and can be purified from the adult brain. Purified aFGF is a mitogen for neuroblasts and promotes the neuritis extension from spinal cord neurons. In addition, aFGF was proved to promote the expression of nerve growth factors on astrocytes in culture.

It was reported in several studies that FGFs had a wide spectrum of effects on neurophysiological activities that were distinct from their mitogenic action within the central nervous system (CNS) in vivo. For instance, when administered into the brain, aFGF provided a protective effect against the degeneration of hippocampal CA1 neuron that was induced by brain ischemia (Sasaki K. et al., *Brain Res. Bull.* 33: 505-511, 1994). FGF1 was reported to have an effect in protecting selective neuronal populations against the neurotoxic effects of molecules involved in the pathogenesis of neurodegenerative disorders such as Alzheimer's disease (Guo, Z., and Mattson, M., *Cereb. Cortex* 10, 50-57, 2000) and HIV encephalitis (Everall, I. P. et al., *J. Neuropathol. Exp. Neurol.* 60, 293-301, 2001).

Native human aFGF polypeptide consisting of 154 amino acids was isolated from a human brain. However, the 19 amino acids from the N-terminal of the human aFGF were identified homogenous with human interleukin-1 (IL-1). The 19 amino acids from the N-terminal of the native human aFGF in common with or similar to the amino acids of IL-1 might cause the same endogenous immuno-response, including activation of macrophages, and modulate cells growth arrest (G. Venkataraman et al., P.N.A.S., 96:3658-63, 1999). Furthermore, it was reported that the pro-inflammatory cytokine IL-1 and FGF-1 (aFGF)/FGF-2 (bFGF) shared the same structural scaffold and competed against the same receptor binding site of tyrosine kinase domains (A. J. Minter et al., J. Cell Physil., 167:229-37, 1996).

Several versions of recombinant human aFGF are commercially available and widely used in various bioassays. For example, recombinant human aFGF having 140 amino acids (R&D, aa 16-155, Catalog Number: 232-FA/CF), recombinant human aFGF having 154 amino acids (R&D, aa 2-155, Catalog Number: 231-BC/CF), recombinant human aFGF having 141 amino acids (Sigma, natural sequence with an additional methionine residue attached to the N-terminus, Catalog Number: F5542). See also, Osakada F et al., Nat Protoc. 2009;4(6):811-24, and Christina Krabbe et al., J. Neurochem. (2009) 110, 1908-1920.

Furthermore, U.S. Pat. No. 7,956,033 (issued in 2011) discloses a modified human aFGF having 135 amino acids exhibiting improved stability, which comprises a native human aFGF shortened by a deletion of a deletion of 20 amino acids from N-terminal of the native human aFGF, and an addition of Alanine (Ala) before the shortened native aFGF.

SUMMARY OF THE INVENTION

In one aspect, the present invention provides a acidic fibroblast growth factor (aFGF) composition, comprising: (i) aFGF of SEQ ID NO: 1, (ii) aFGF of SEQ ID NO: 1 having an N-terminal phosphogluconoylation, (iii) aFGF of SEQ ID NO: 1 having an N-terminal gluconoylation, (iv) aFGF of SEQ ID NO: 2 and (v) aFGF of SEQ ID NO: 3, or a combination thereof.

In one embodiment of the present invention, the aFGF composition has the following high performance ion-exchange chromatography (HPIEC) peaks:

| Peak | Retention time (min) |
|---|---|
| 1 | 18.2 |
| 2 | 18.5 |
| 3 | 19.1 |
| 4 | 19.4 |
| 5 | 19.9 | wherein said HPIEC is conducted at the condition of:
Flow rate: 0.5 mL/min
Sample amount: 100 μL
Column: ProPac Ion Exchange Column
Absorbance: 220-280 nm
Elution profile:
Buffer A: 20 mM MES, pH 6.0-8.0
Buffer B: 20 mM MES+1M NaCl, pH 6.0-8.0

| Time (min) | Buffer A (%) | Buffer B (%) |
|---|---|---|
| 0 | 95 | 5 |
| 5 | 95 | 5 |
| 15 | 45 | 55 |
| 25 | 40 | 60 |
| 30 | 20 | 80 |
| 40 | 95 | 5 |

In another aspect, the present invention provides a modified acidic fibroblast growth factor (aFGF) which has an N-terminal phosphogluconoylation or gluconoylation.

According to the present invention, the aFGF composition and the modified aFGF exhibit an improved specific activity as compared to the human aFGF of SEQ ID NO: 1, or a wild type human aFGF.

BRIEF DESCRIPTION OF THE DRAWINGS

The foregoing summary, as well as the following detailed description of the invention, will be better understood when read in conjunction with the appended drawing. In the drawings:

FIG. 2A shows the HPIEC profile of aFGF135, FIG. 2B shows the HPIEC profile of aFGF140, and FIG. 2C shows the HPIEC profile of aFGF154.

DESCRIPTION OF THE INVENTION

Figure 1:
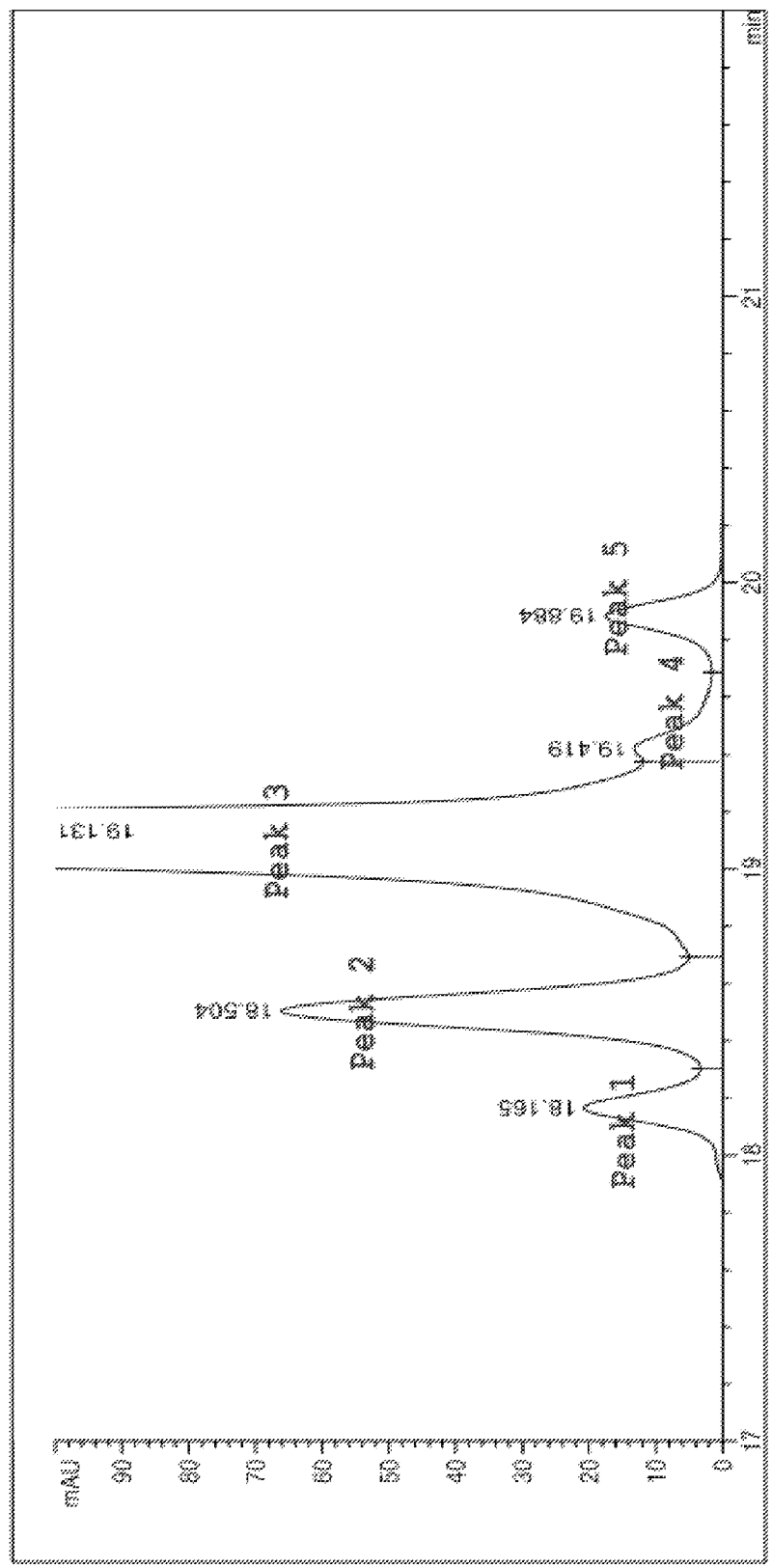
FIG. 1 shows the HPIEC profile of an aFGF135 (SEQ ID NO: 1) sample.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

As used herein, the term "acidic fibroblast growth factor" or "aFGF" refers to a heparin-dependent mitogen and it can strongly bind on all four known FGF receptors and their spliced form, including any type of aFGFs, preferably human aFGFs, which may be native, a wild type or modified aFGF. In one preferred embodiment, the aFGF has the amino acid sequence of SEQ ID NO: 1, as disclosed in U.S. Pat. No. 7,956,033, which is herein incorporated by reference.

It was unexpectedly found in the present invention that a modified aFGF having an N-terminal phosphogluconoylation or gluconoylation exhibits an improved specific activity as compared with aFGF without phosphogluconoylation and gluconoylation, or a wild type aFGF.

In an embodiment of the invention, the aFGF has the amino acid of SEQ ID NO: 1.

In one preferred example of the invention, the modified aFGF of the invention is performed by an addition of phosphogluconoylation or gluconoylation to the aFGF, preferably human aFGF, most preferably the human aFGF of SEQ ID NO: 1. It was unexpectedly found in the present invention that the modified human aFGF has a superior specific activity.

As used herein, the term "phosphogluconoylation" refers to a modification or chemical modification to a molecule (such as a protein) by adding one or more 6-phosphogluconoyl groups.

The term "phosphogluconoylation" as used herein, refers a modification or chemical modification to a molecule (such as a protein) by adding one or more phosphogluconoyl groups. In one embodiment of the present invention, the phosphogluconoylation of the aFGF is performed by an addition of a 6-phosphogluconoyl group to the aFGF.

The term "gluconoylation" as used herein, refers to a modification or chemical modification to a molecule (such as a protein) by adding one or more gluconoyl groups. In one example of the invention, the gluconoylation of the aFGF is performed by an addition of a 6-gluconoyl group to the aFGF. In addition, according to the invention, the aFGF with gluconoylation may come from a dephosphorylation of the aFGF with phosphogluconoylation. Accordingly in another example of the invention, the gluconoylation of the aFGF is performed by an addition of a 6-phosphogluconoyl group to the aFGF and then a dephosphorylation. According to the present invention, both a modified human aFGF with gluconoylation and a modified human aFGF with phosphogluconoylation have improved specific activity as compared with aFGF without phosphogluconoylation and gluconoylation, or a wild type aFGF.

Phosphogluconoylation or gluconoylation of a protein may be performed through a native process or a chemical modification, such as a synthetic method. On the other hand, since gluconoylation or phosphogluconoylation (such as α-N-6- phosphogluconoylation) may occur as post-translational modification to proteins expressed in *Escherichia coli* ("*E. coli*") (Geoghegan, et al., Anal. Biochem. 267:169-184 (1999); Kim et al., Acta Crystallographica Section D-Biological Crystallography 57:759-762 (2001); Yan, et al. Biochemical & Biophysical Research Communications 262: 793-800 (1999) "Yan et al. I;" Yan, et al., Biochemical & Biophysical Research Communications 259:271-282 (1999) "Yan et al. II"), the phosphogluconoylated or gluconoylated proteins may be produced by expression in appropriate *E. coli* strain.

It was reported that such post-translational modification may adversely effect activity, stability, structure, or immunogenicity of the expressed protein. However, as surprisingly found in the present invention, the phosphogluconoylated or gluconoylated human aFGF exhibits an improved specific activity as compared to the human aFGF without phosphogluconoylation and gluconoylation, or a wild type human aFGF. In one embodiment, the human aFGF is a human aFGF of SEQ ID NO: 1.

As used herein, "aFGF specific activity" or "specific activity" refers to an aFGF activity, as measured by a bioassay, of a unit amount of sample.

In another aspect, the present invention provides a acidic fibroblast growth factor (aFGF) composition, comprising: (i) aFGF of SEQ ID NO: 1, (ii) aFGF of SEQ ID NO: 1 having an N-terminal phosphogluconoylation, (iii) aFGF of SEQ ID NO: 1 having an N-terminal gluconoylation, (iv) aFGF of SEQ ID NO: 2 and (v) aFGF of SEQ ID NO: 3, or a combination thereof.

aFGF of SEQ ID NO: 2 is an aFGF of SEQ ID NO: 1 modified by replacing the asparagine at position 101 with a lysine. aFGF of SEQ ID NO: 3 is an aFGF of SEQ ID NO: 1 modified by replacing the asparagine at position 2 with a lysine.

In one embodiment of the present invention, the aFGF composition consists of: (i) aFGF of SEQ ID NO: 1, (ii) aFGF of SEQ ID NO: 1 having an N-terminal phosphogluconoylation, (iii) aFGF of SEQ ID NO: 1 having an N-terminal gluconoylation, (iv) aFGF of SEQ ID NO: 2 and (v) aFGF of SEQ ID NO: 3, or a combination thereof.

In one embodiment of the present invention, the aFGF composition has the following HPIEC peaks:

| Peak | Retention time (min) |
|---|---|
| 1 | 18.2 |
| 2 | 18.5 |
| 3 | 19.1 |
| 4 | 19.4 |
| 5 | 19.9 | wherein said HPIEC is conducted at the condition of:
Flow rate: 0.5 mL/min
Sample amount: 100 μL
Column: ProPac Ion Exchange Column
Absorbance: 220-280 nm
Elution profile:
    Buffer A: 20 mM MES, pH 6.0-8.0
    Buffer B: 20 mM MES+1M NaCl, pH 6.0-8.0

| Time (min) | Buffer A (%) | Buffer B (%) |
|---|---|---|
| 0 | 95 | 5 |
| 5 | 95 | 5 |
| 15 | 45 | 55 |
| 25 | 40 | 60 |

-continued

| Time (min) | Buffer A (%) | Buffer B (%) |
|---|---|---|
| 30 | 20 | 80 |
| 40 | 95 | 5 |

The aFGF composition of the present invention shows an improved specific activity as compared to human aFGF of SEQ ID NO: 1, or a wild type human aFGF.

EXAMPLES

Example 1

Expression and Isolation of the Modified Human aFGF of SEQ ID NO: 1 ("aFGF135")

A vector, pET3c-haFGF, for expression of aFGF135 was constructed as described in U.S. Pat. No. 7,956,033, the disclosure of which is incorporated herein by reference in its entirety.

The pET3c-haFGF was amplified and then transformed to *E. coli* BL21 (DE3) (Novagen, Germany) competent cells. The *E. coli* colonies resistant to ampicillin were cultured and amplified in LB medium to $OD_{600}$=0.3 before induction with IPTG. After an incubation for 16 hours (±2 hours), the bacteria were collected and centrifuged with 5000 rpm to remove the supernatant. The bacteria as collected were washed with PBS twice, then lysed with a high pressure homogenizer; and then flowed through a sieve with a pore size of 0.22 μm. The filtered medium was ready for isolation of protein.

The peptide of the aFGF135 was isolated by three kinds of chromatography columns: (1) a cation exchange chromatography; (2) an affinity chromatography; and (3) a size exclusion chromatography. The buffer used for the aforementioned columns was phosphate solution ($Na_2PO_4$: $NaHPO_3$=51: 49 with 0.1% EDTA-Na, pH 6.0-8.0).

Example 2

HPIEC (High Performance Ion-Exchange Chromatography) of the Expressed Proteins

The isolated peptide composition as obtained in Example 1 was subjected to HPIEC analysis. The chromatography condition is as follows: Mobile Phase: Buffer A-20mM MES, pH 6.0-8.0, Buffer B-20 mM MES+1 M NaCl, pH 6.0-8.0; Column: ProPac Ion Exchange Column; Absorbance: 220-280 nm; Inj. Volume (Sample amount): 100 μL; Flow rate: 0.5 mL/min; Time: 45 min.; and Temp.: 25° C., with the gradient curve of:

| Time (min) | Buffer A (%) | Buffer B (%) |
|---|---|---|
| 0 | 95 | 5 |
| 5 | 95 | 5 |
| 15 | 45 | 55 |
| 25 | 40 | 60 |
| 30 | 20 | 80 |
| 40 | 95 | 5 |

A bioassay on Balb/3T3 cell proliferation is performed as described below. Select Balb/3T3 cells which grow well, and calculate the concentration of the cells. A 96-well plate is used in the assay, wherein 60 wells (B2 to G11) are loaded with assay samples, and other surrounding wells are loaded with sterile PBS. The cells are seeded on the plate at a density of $2\times10^4$ cells/well in a medium of RPMI-1640+ 10% FBS, and cultured under 37° C., 5% CO2 for 24±2 hours. Prepare a sample dilution buffer of RPMI-1640 medium+0.5% FBS. A standard aFGF composition as obtained in Example 1 is diluted to 16 unit/ml using the sample dilution buffer (RPMI-1640 medium+0.5% FBS), and serially diluted by 2 times concentration to obtained at least 6 serially diluted samples. Subsequently, remove the medium in the 96-well plate, add 100 μL of the samples to each of the wells, and culture under 37° C., 5% CO2 for 24±2 hours. For the activity measurement, first place the plate under room temperature for 15 minutes, and then add 100 μL of luminescent reagent to each well for reaction of 30 minutes. Lastly, the luminescent signal is detected and the activity is calculated by Parallel-Line Assay.

The results are shown in FIG. 1 and Table 1 below. Five main peaks were observed at the retention times (min.) around 18.165, 18.504, 19.131, 19.419, and 19.884, respectively.

TABLE 1

| | | Batch No. of aFGF 135 | | | |
|---|---|---|---|---|---|
| Tests | | P1 | P2 | P3 | P5 |
| HPIEC | Peak 1 | 6.46 | 6.46 | 6.32 | 3.02 |
| (%) | Peak 2 | 7.29 | 7.32 | 7.14 | 9.63 |
| | Peak 3 | 83.10 | 83.09 | 83.39 | 83.65 |
| | Peak 4 | 1.37 | 1.31 | 1.31 | 1.19 |
| | Peak 5 | 1.77 | 1.82 | 1.86 | 2.52 |
| | Peaks 1~5 | 100 | 100 | 100 | 100 |
| HPSEC | | 100 | 100 | 100 | 100 |
| (% monomer) | | | | | |
| HPLC-RP | | 100 | 100 | 100 | 100 |
| (% main peak) | | | | | |
| Bioassay (unit/mL) | | 17240 | 17840 | 18780 | 22040 |

Example 3

Comparison of HPIEC Profiles of Different Human aFGFs

Three different human aFGFs, aFGF135, aFGF140 and aFGF154, were tested in this study. aFGF135 of SEQ ID NO: 1 is prepared as described in Example 1 above. aFGF140 (having 140 amino acids) is R&D Recombinant Human FGF acidic aa 16-155 (Catalog Number: 232-FA/ CF) purchased from R&D Systems, Inc., Minneapolis, Minn. 55413 USA. aFGF154 (having 154 amino acids) is R&D Recombinant Human FGF acidic aa 2-155 (Catalog Number: 231-BC/CF) purchased from R&D Systems, Inc., Minneapolis, Minn. 55413 USA. The chromatography condition is the same as set forth in Example 2 above.

Figure 2A:
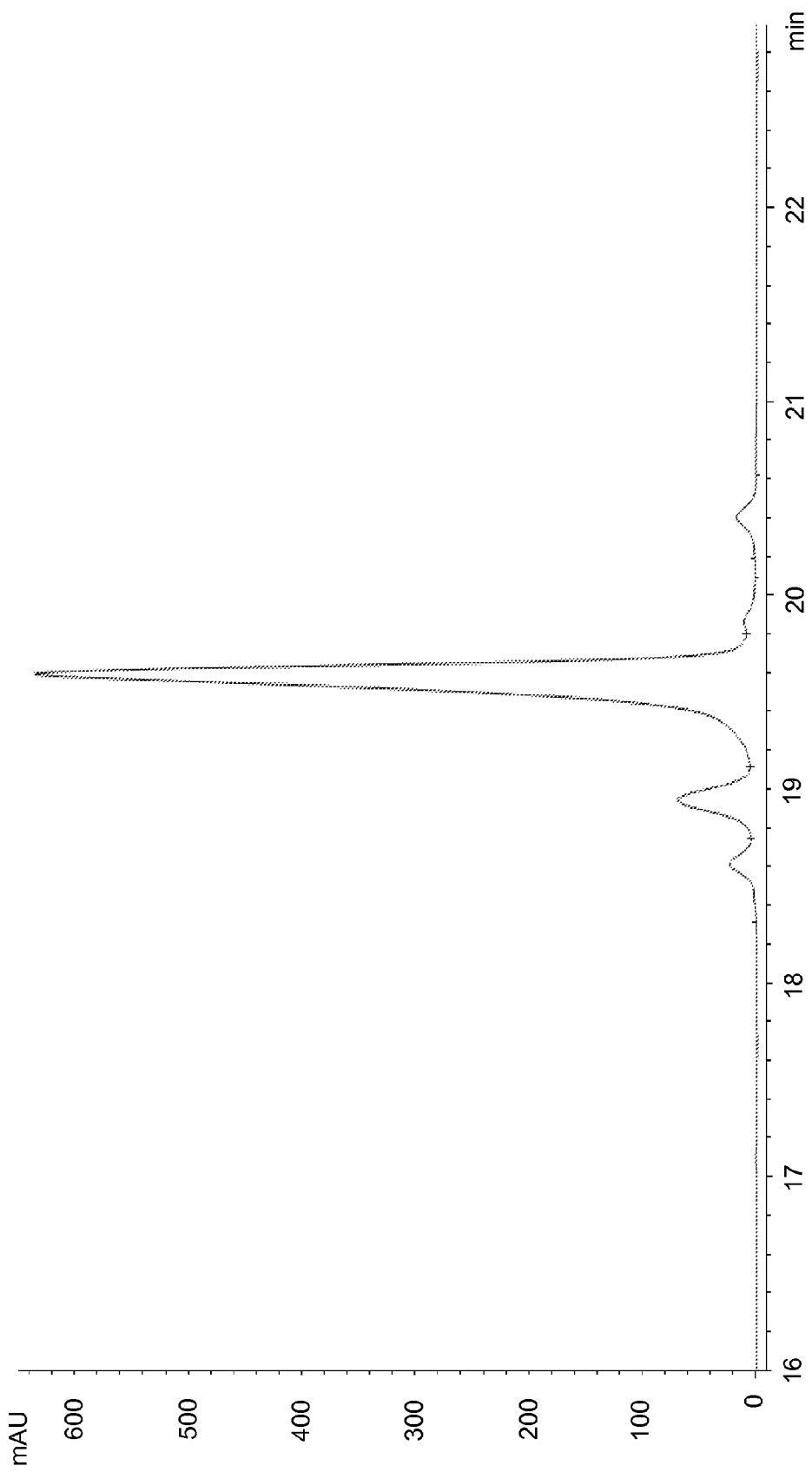
FIG. 2A-2C provide HPIEC profiles of aFGF135, aFGF140 and aFGF154.
Figure 2B:
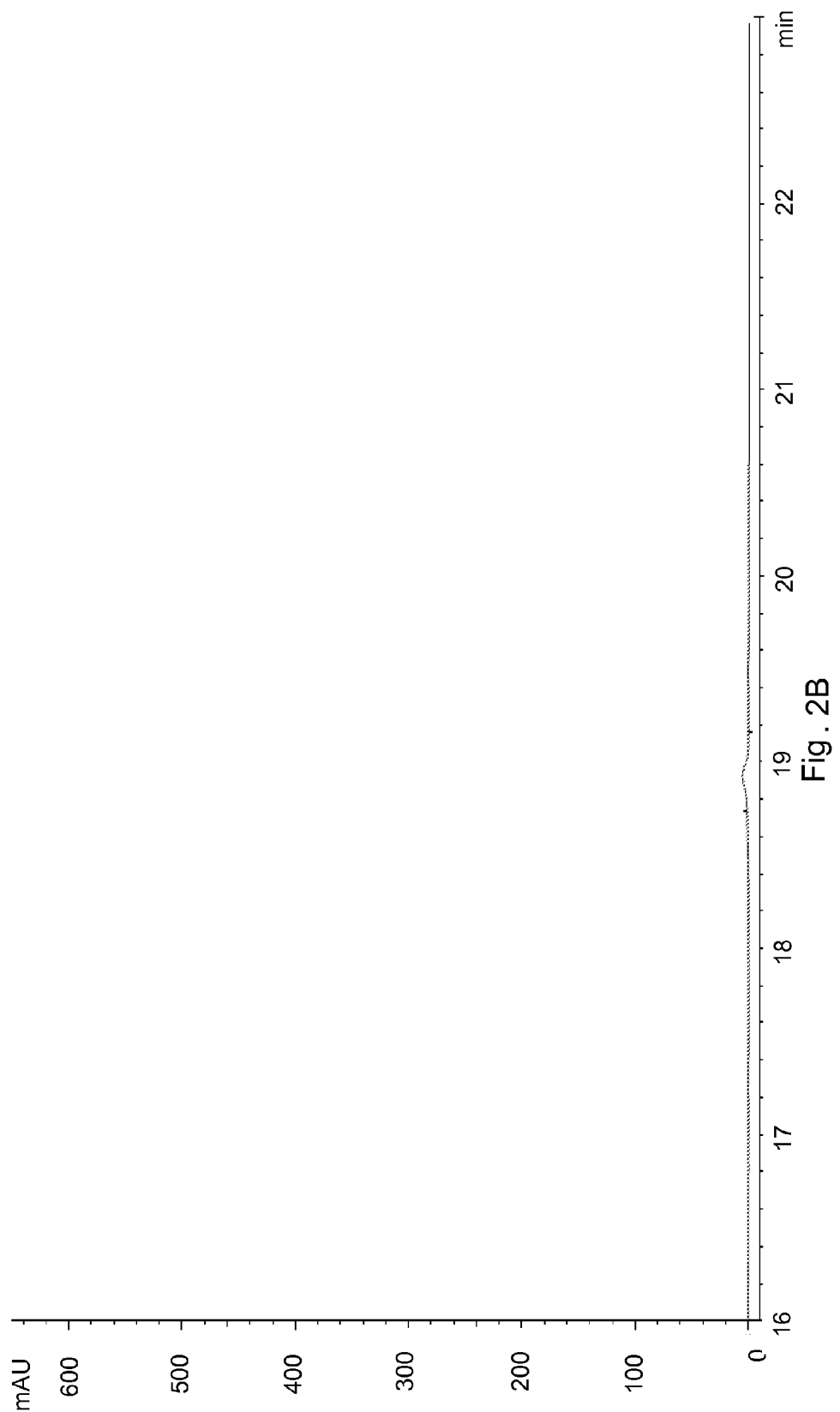
Figure 2C:
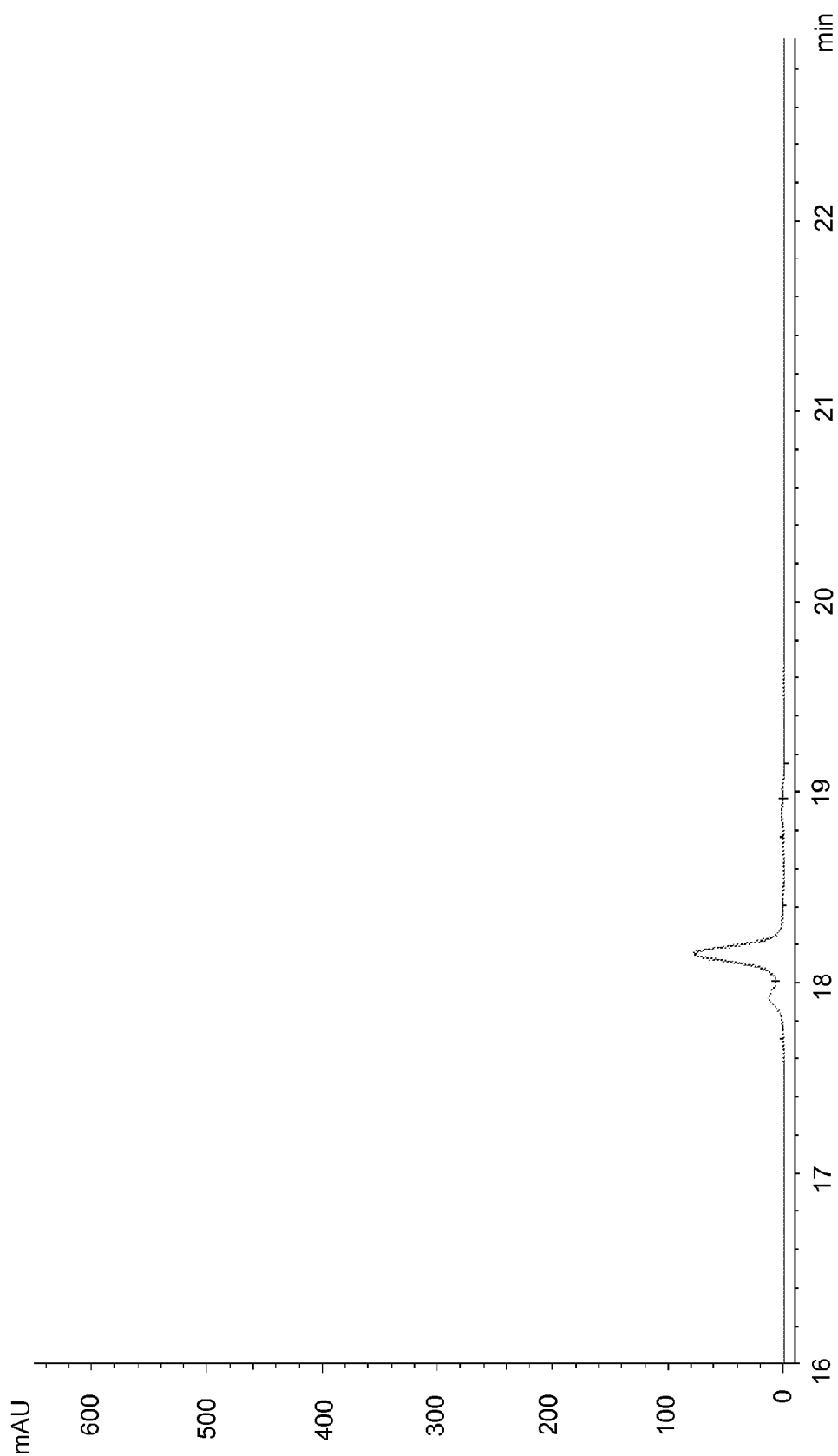

The results are provided in FIG. 2A-2C. FIG. 2A shows the HPIEC profile of aFGF135, FIG. 2B shows the HPIEC profile of aFGF140, and FIG. 2C shows the HPIEC profile of aFGF154. As shown in FIG. 2A-2C, aFGF135, aFGF140 and aFGF154 have very different HPIEC profiles.

Example 4

Identification of the HPIEC Peaks of aFGF135 by LC-MS/MS and Comparison of their Specific Activities 1. Arg-C digestion: Samples from each peak were first concentrated by 3kDa cut-off Amicon Ultra Centrifugal Filter. All 16 samples (10 μg, HPIEC Peaks 1, 2, 4 and 5 from the four lots) were diluted with 50 mM ammonium bicarbonate buffer to 100 μL. Then all protein samples were denatured with 6 M urea and reduced with 1 μL 1 M DTT at 37° C. for 1 hour. Alkylation was conducted using 10 μL 0.5 M IAM for 30 mM in dark at room temperature. The resulting haFGF protein was diluted with 50 mM ABC buffer and then digested by 0.5 μg Arg-C (protein: enzyme=20: 1) at 37° C. for 17 hours. After digestion, all samples were desalted using Zip Tip (Millipore), dried by speedvac, and re-dissolved with 0.1% FA for LC-MS/MS analysis.

2. LC-MS/MS analysis: The digested samples (0.5 μg) were analyzed with Q-Exactive mass spectrometer coupled with Ultimate 3000 RSLC system. The LC separation was performed using the C18 column (Acclaim PepMap RSLC, 75 μm×150 mm, 2 μm, 100 Å) with the gradient shown below:

| Time (min) | A % | B % | Flow (μL/min) |
| --- | --- | --- | --- |
| 0 | 99 | 1 | 0.25 |
| 7 | 99 | 1 | 0.25 |
| 47 | 60 | 40 | 0.25 |
| 55 | 10 | 90 | 0.25 |
| 65 | 10 | 90 | 0.25 |
| 70 | 99 | 1 | 0.25 |
| 75 | 99 | 1 | 0.25 |

(Mobile phase A: 5% ACN/0.1% FA; Mobile phase B: 95% ACN/0.1% FA) Full MS scan was performed with the range of m/z 380-1800, and the ten most intense ions from MS scan were subjected to fragmentation for MS/MS spectra. Raw data were processed into peak lists by Proteome Discoverer 1.4 for Mascot database search.

3. Database search parameters: Database search was performed with Mascot 2.4.0. The parameters used were as follows:

Database: sequence provided by sponsor
Enzyme: Arg-C*
Variable modifications: phosphogluconoylation (Protein N-term); gluconoylation (Protein N-term); Methylation (Asn, Ala and Lys)
Peptide mass tolerance: ±10 ppm
Fragment mass tolerance: ±0.02 Da
Max missed cleavages: 5
Instrument type: ESI-TRAP
Ion cut-off score: 30
Arg-C*: The enzyme has been shown to cleave at the carboxyl side of arginyl residues, Lys-Lys and Lys-Arg bonds.

3. Results:

TABLE 2

LC-MS/MS results

| Sample | No | Position | Observed | Mr (expt) | Mr (calc) | ppm | MC | Score | Peptide |
| --- | --- | --- | --- | --- | --- | --- | --- | --- | --- |
| Peak 1 | P1 | 1-19 | 842.0734 | 2523.1983 | 2523.1981 | 0.06 | 1 | 57 | -.ANYKKPKLLYCSNGGHFLR.I + phosphogluconoylation [+258.0141 Da at Protein N-term] |
|  | P2 | 1-19 | 842.0728 | 2523.1966 | 2523.1981 | -0.60 | 1 | 58 | -.ANYKKPKLLYCSNGGHFLR.I + phosphogluconoylation [+258.0141 Da at Protein N-term] |
|  | P3 | 1-19 | 842.0723 | 2523.1952 | 2523.1981 | -1.17 | 1 | 59 | -.ANYKKPKLLYCSNGGHFLR.I + phosphogluconoylation [+258.0141 Da at Protein N-term] |
|  | P5 | 1-19 | 842.0714 | 2523.1924 | 2523.1981 | -2.26 | 1 | 71 | -.ANYKKPKLLYCSNGGHFLR.I + phosphogluconoylation [+258.0141 Da at Protein N-term] |
| Peak 2 | P1 | 1-19 | 815.4175 | 2443.2306 | 2443.2318 | -0.47 | 1 | 62 | -.ANYKKPKLLYCSNGGHFLR.I + gluconoylation [+178.0477 Da at Protein N-term] |
|  | P2 | 1-19 | 815.4175 | 2443.2308 | 2443.2318 | -0.40 | 1 | 62 | -.ANYKKPKLLYCSNGGHFLR.I + gluconoylation [+178.0477 Da at Protein N-term] |
|  | P3 | 1-19 | 815.4157 | 2443.2253 | 2443.2318 | -2.65 | 1 | 70 | -.ANYKKPKLLYCSNGGHFLR.I + gluconoylation [+178.0477 Da at Protein N-term] |
|  | P5 | 1-19 | 815.4155 | 2443.2248 | 2443.2318 | -2.87 | 1 | 58 | -.ANYKKPKLLYCSNGGHFLR.I + gluconoylation [+178.0477 Da at Protein N-term] |
| Peak 4 | P1 | 96-107 | 735.9331 | 1469.8517 | 1469.8507 | 0.67 | 0 | 78 | K.KHAEKNWFVGLK.K + [+14.0520 at N6] |
|  | P2 | 96-107 | 735.9321 | 1469.8496 | 1469.8507 | -0.74 | 0 | 67 | K.KHAEKNWFVGLK.K + [+14.0520 at N6] |
|  | P3 | 96-107 | 735.9304 | 1469.8463 | 1469.8507 | -2.99 | 0 | 73 | K.KHAEKNWFVGLK.K + [+14.0520 at N6] |
|  | P5 | 96-107 | 735.9299 | 1469.8452 | 1469.8507 | -3.73 | 0 | 68 | K.KHAEKNWFVGLK.K + [+14.0520 at N6] |
| Peak 5 | P1 | 1-19 | 760.7521 | 2279.2346 | 2279.2361 | -0.65 | 1 | 59 | -.ANYKKPKLLYCSNGGHFLR.I + [+14.0520 ay N2] |
|  | P2 | 1-19 | 760.7521 | 2279.2346 | 2279.2361 | 0.65 | 1 | 53 | -.ANYKKPKLLYCSNGGHFLR.I + [+14.0520 ay N2] |
|  | P3 | 1-19 | 760.7507 | 2279.2302 | 2279.2361 | -2.58 | 1 | 42 | -.ANYKKPKLLYCSNGGHFLR.I + [+14.0520 ay N2] |

TABLE 2-continued

LC-MS/MS results

| Sample | No | Position | Observed | Mr (expt) | Mr (calc) | ppm | MC | Score | Peptide |
|---|---|---|---|---|---|---|---|---|---|
| | P5 | 1-19 | 760.7507 | 2279.2302 | 2279.2361 | -2.58 | 1 | 59 | -.ANYKKPKLLYCSNGGHFLR.I + [+14.0520 ay N2] |

"Position" indicates the number of residue of haFGF.
"Observed" indicates the observed m/z value in the survey scan, while "Mr (expt)", "Mr (calc)", "ppm" indicate the experimental molecular weight (MW), calculated MW, and the difference between observed MW and theoretical MW respectively.
MC stands for missed cleavage.
Scores are the peptide ion score directly reported from Mascot database search engine.

Samples from Peak 3 were found to be aFGF135 without modification through LC-MS. MS.

TABLE 3

Modifications of aFGF

| Sample | Modification |
|---|---|
| Peak 1 | Phosphogluconoylation at N-terminus |
| Peak 2 | Gluconoylation at N-terminus |
| Peak 3 | — |
| Peak 4 | Amino acid substitution- Asn 101 to Lys |
| Peak 5 | Amino acid substitution- Asn 2 to Lys |

Figure 3:
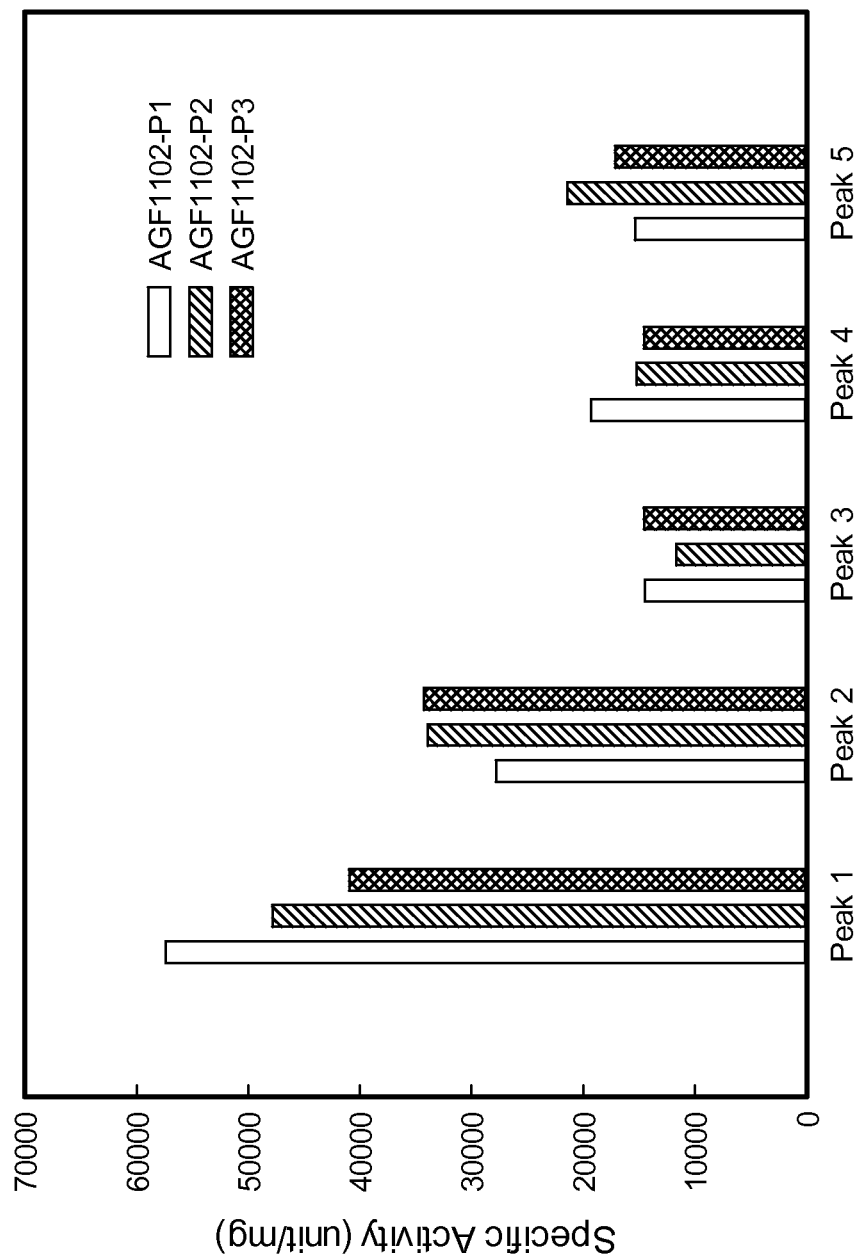
FIG. 3 shows specific activities of samples from the five peaks of the HPIEC profile of an aFGF135 sample.

Further, the specific activities of samples from five peaks were compared. A bioassay on Balb/3T3 cell proliferation is performed as described in Example 2 above. As shown in FIG. 3, samples from peaks 1 and 2 exhibit higher specific activities compared to that of the sample from peaks 3, 4 or 5.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A peptide consisting of the modified acidic fibroblast growth factor (aFGF) of SEQ ID NO: 1 where the N-terminal is phosphogluconoylated.

2. A peptide consisting of the modified acidic fibroblast growth factor (aFGF) of SEQ ID NO: 1 where the N-terminal is gluconoylated.

3. A peptide consisting of the modified acidic fibroblast growth factor (aFGF) of SEQ ID NO: 2.

4. A peptide consisting of the modified acidic fibroblast growth factor (aFGF) of SEQ ID NO: 3.

* * * * *